(12) United States Patent
Freeman et al.

(10) Patent No.: US 6,590,217 B1
(45) Date of Patent: Jul. 8, 2003

(54) ULTRAVIOLET STERILIZATION DEVICE

(75) Inventors: Timothy A. Freeman, Toronto (CA); Timothy Hing Yan Chung, Etobicoke (CA); Douglas L. Newton, Toronto (CA); Victor Hilario, Mississauga (CA)

(73) Assignee: CFM Corporation (CA)

( * ) Notice: Subject to any disclaimer, the term of this patent is extended or adjusted under 35 U.S.C. 154(b) by 0 days.

(21) Appl. No.: 10/180,172

(22) Filed: Jun. 26, 2002

Related U.S. Application Data

(60) Provisional application No. 60/357,614, filed on Feb. 15, 2002.

(51) Int. Cl.[7] ................................................ G01N 21/00
(52) U.S. Cl. ........................ 250/435; 250/438; 250/436
(58) Field of Search ................................. 250/431, 436, 250/438

(56) References Cited

U.S. PATENT DOCUMENTS 5,247,178 A * 9/1993 Ury et al. .................. 250/438

* cited by examiner

Primary Examiner—John R. Lee
Assistant Examiner—Phillip A Johnston
(74) Attorney, Agent, or Firm—Baniak Pine & Gannon

(57) ABSTRACT

An apparatus for irradiation of a fluid with UV light includes a tubular body consisting of UV-permeable material. The body includes a fluid chamber and openings for passage of fluid. A UV source is provided to subject the chamber to the UV light. A wiper is centrally supported in the body to clean the inner surface of the body. Light baffles define an irradiated section of the chamber to prevent light penetration beyond the irradiated section while permitting the fluid to flow through. The apparatus is provided as a component in a housing having a modular design. The modules include a back cover for surface mounting. The body is mounted to the back cover. An inner cover is attached to the back cover. The inner cover includes the UV source and modular electronics. A front cover is attached to the inner and back cover.

24 Claims, 12 Drawing Sheets

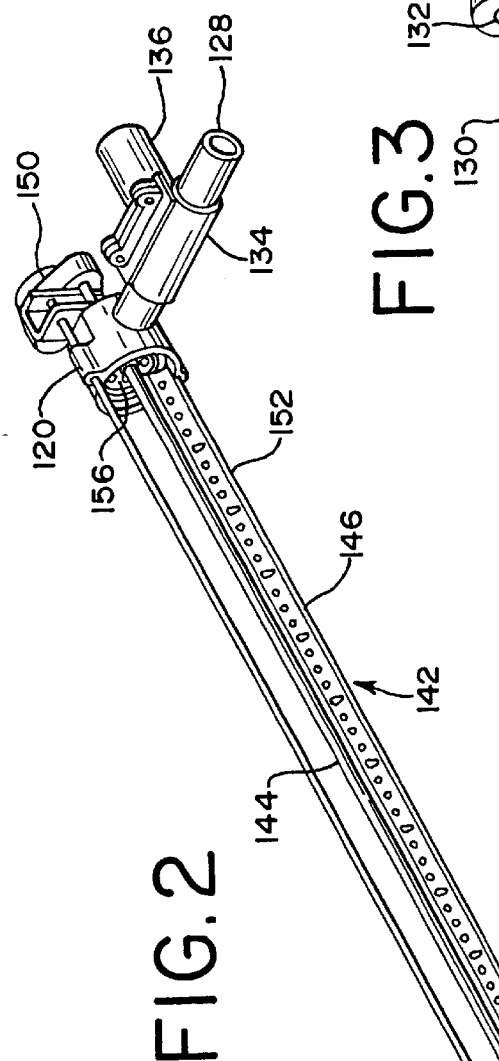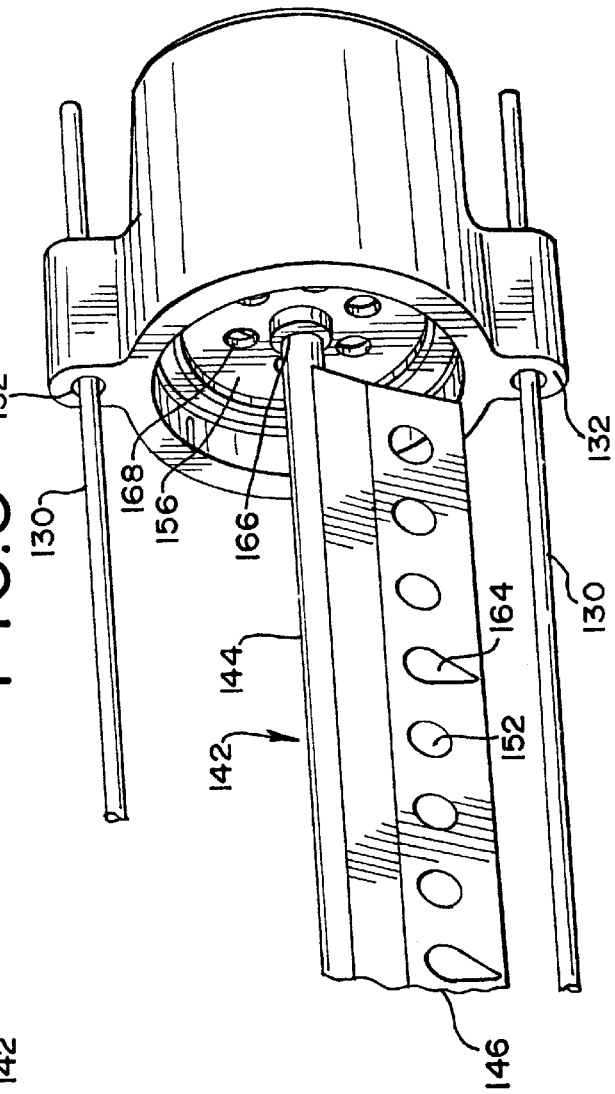

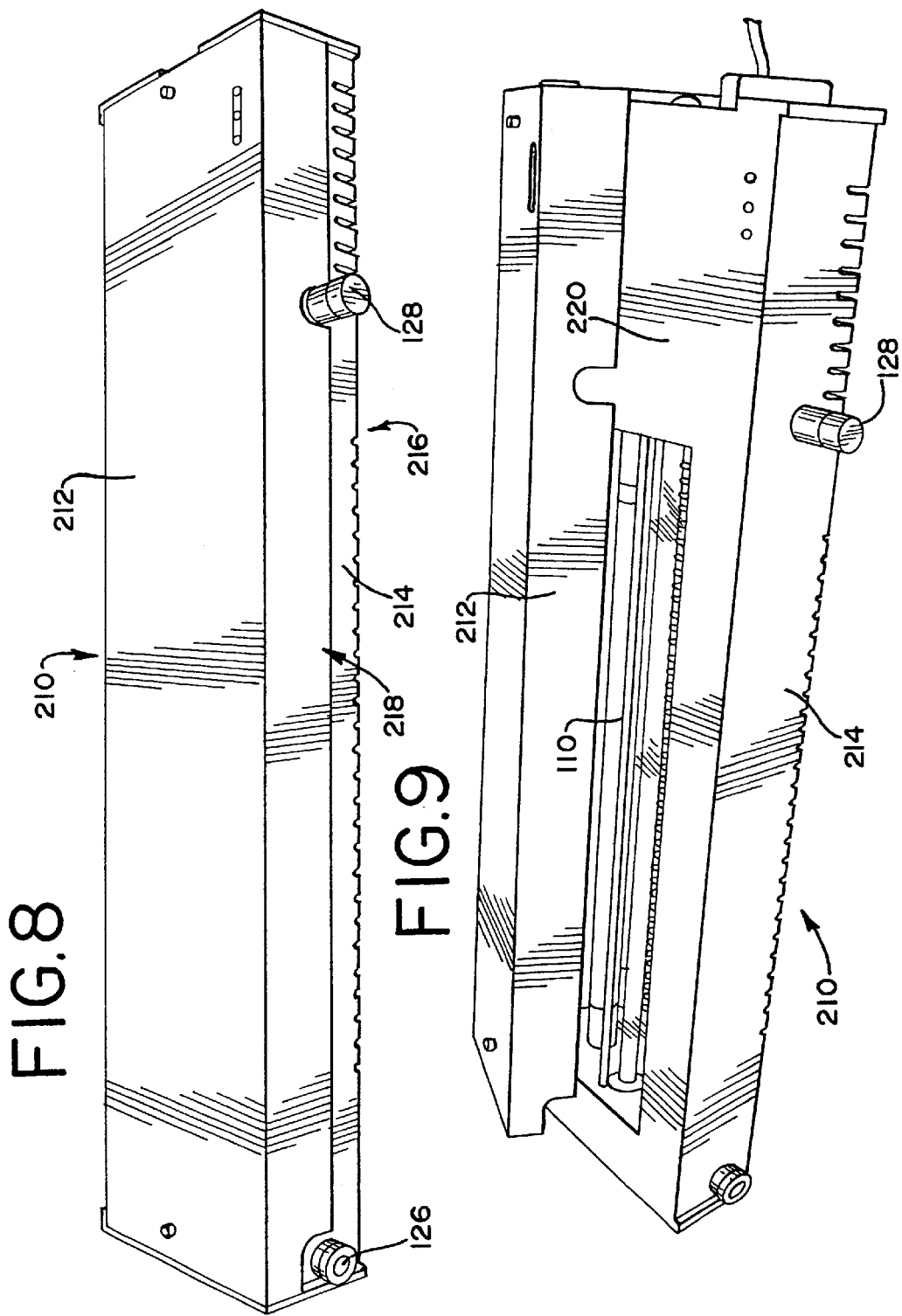

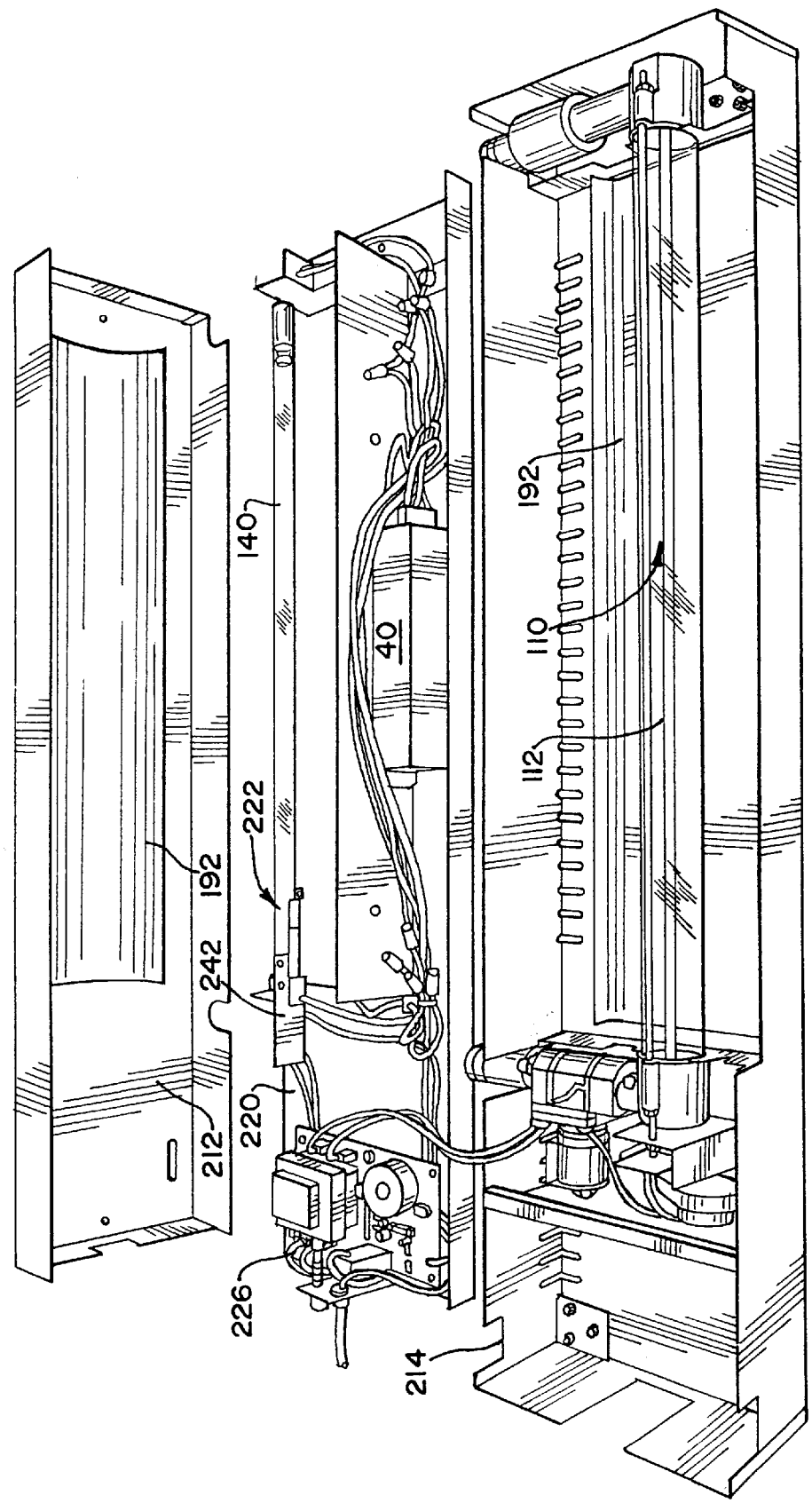

ULTRAVIOLET STERILIZATION DEVICE

This application claims the benefit of U.S. Provisional Application No. 60/357,614 filed Feb. 15, 2002.

FIELD OF THE INVENTION

This invention relates to an apparatus for subjecting fluids to ultraviolet (UV) light. The apparatus may be used for water sterilization and is intended for Point-of-Entry use. More particularly it relates to an apparatus for use in water purification having improved effectiveness through the employment of a self-cleaning mechanism to maintain a desired degree of transmittance of ultraviolet radiation through an ultraviolet transparent quartz tube for ultraviolet lamps. The apparatus includes an efficient arrangement of light shielding baffles to protect UV sensitive components from the UV light. The apparatus is provided as a component in a housing having a modular design.

BACKGROUND OF THE INVENTION

Point-of-Entry ultraviolet water sterilization devices typically include a pressure vessel including a stainless steel cylinder enclosing a smaller concentric quartz light transmission tube. Within the quartz tube is a tubular discharge lamp emitting light with wavelengths typically centered around 254 nm, which is referred to as ultraviolet light or ultraviolet radiation. Ultraviolet (UV) light represents a section of the overall electromagnetic spectrum of light, extending from the blue end of the visible at about 400 nm to a region of about 100 nm.

Water to be exposed to the light from the lamp is passed between the interior surface of the steel cylinder and the exterior surface of the light transmission tube. One important limitation to this type of device is that the exterior surface of the quartz tube becomes fouled with inactivated biological contaminants in the water as well as minerals at least in part due to a photochemical reaction upon exposure to the light of the lamp. Due to the arrangement of the discharge lamp contained in a quartz sheath, the foulants collect on the exterior of the quartz tube. The foulants cause a reduced transmission of ultraviolet light through the light transmission tube, which results in a reduced efficacy of the device. This requires that the device be disassembled periodically for cleaning of the quartz tube to maintain its effectiveness.

To reduce maintenance and downtime, automatic wiping mechanisms have been tried on these systems with limited success. U.S. Pat. No. 5,266,280 discloses a system of radially mounted brushes that act to wipe the external surface of the quartz sheath. This costly mechanism is difficult to actuate and to provide adequate sealing for the power transmission shaft connected to the motor outside of the steel cylinder of the pressure vessel. Also described are a number of other similar external wipers, which have varying amounts of effectiveness. Cleaning the tube in this manner is cumbersome and compromises the irradiation dosage of the device because the gap between the outer wall of the quartz sheaf and the inner wall of the pressure vessel must be increased to accommodate the wiper resulting in a larger dosage gradient across the laminar fluid cross section.

Attempts have been made at providing means to conduct fluid through a quartz tube with UV emitting lamps arranged external to the quartz tube and with a wiper mechanism acting to clean the inside walls of the tube. These attempts have failed primarily due to material degradation. The ultraviolet light emitted by germicidal lamps causes degradation of some form in all polymer-based materials. Many components used in the construction of an internal automated wiper system must be polymer-based for friction reduction, manufacturability and sealing-performance reasons. U.S. Pat. No. 5,266,280 describes a number of UV resistant materials such as halogenated polyolefins, urethane, synthetic rubber and high-density polypropylene, all of which are susceptible to being degraded by UV light. Some polymeric materials exist which resist UV degradation. However, when they are exposed to UV radiation centered around 254 nm, and are provided in contact with the fluid being sterilized, will leach small doses of volatile organic compounds. This defeats the purpose of purification. Materials certified by government organizations for use with potable water are tested without irradiation of UV light and many polymers in this category are found to be non-compliant after irradiation. For this reason it is unacceptable to simply claim compliance for potable water of materials used in irradiated locations of UV sterilization devices as is typically done.

U.S. Pat. No. 4,002,918 discloses a device of similar arrangement for the purpose of "the irradiation of fluids to initiate chemical reactions", but describes wiper materials as being plastic, which are unacceptable for ultraviolet water sterilization applications. There is no mention of shielding materials from harmful ultraviolet light to prevent the leaching of volatile organic compounds, which has been observed to be a critical factor in the design of ultraviolet water sterilization devices.

There is a demand for a UV water purification device that combines superior performance and low maintenance costs. The present invention satisfies the demand.

SUMMARY OF THE INVENTION

A preferred embodiment of the invention is illustrated with respect to an ultraviolet water purification device or reactor with a novel arrangement of components and materials that provides superior performance and serviceability and yet still allows manufacturability at reasonable cost and by relatively simple means.

According to an aspect of the invention, an apparatus that employs plates formed of a material impervious to ultraviolet radiation on all wavelengths, which acts to shield other components such as rubber and polymer-based seals and bearings from the harmful effects of direct ultraviolet irradiation.

The apparatus includes a tubular body, which may be a quartz tube for conducting fluid therethrough having an internally mounted wiper for the continuous cleaning of an inside surface of the tubular body. Potentially biologically contaminated fluids are irradiated by at least one radiation source including at least one elongated discharge lamp mounted externally with respect to the fluid-conducting tubular body. The wiper is formed of stainless steel or other UV-impervious materials. The wiper may include a rectangular elongate blade mounted to a shaft extending along the long axis of the apparatus. The blade may be provided with one or more holes for increased light penetration and for the production of turbulence. The blade may include slits formed therein, for stress relief of the blade, which extend perpendicular to the axis of the shaft. The radiation source may be surrounded with high-efficiency reflectors designed to concentrate light on the central axis of the fluid being conducted through the tubular body.

One embodiment of the apparatus of the present invention provides irradiation of a fluid with UV light and includes a tubular body consisting of a UV-permeable material. The tubular body includes an inner surface defining a fluid chamber and open first and second ends for ingress and egress of the fluid through the fluid chamber. At least one UV radiation source is provided and is so arranged relative to the tubular body as to subject the chamber to the UV light. A wiper is centrally supported in said body for rotation therein, sized and shaped to contact the inner surface. First and second light baffles are positioned inside the tubular body adjacent respective first and second ends and define an irradiated section of the fluid chamber therebetween to prevent UV light penetration beyond the irradiated section of the fluid chamber while permitting the fluid to flow through the apparatus.

The apparatus is provided as a component in a housing having a modular design. One aspect of the invention provides an apparatus for irradiation of a fluid with UV light including a back cover for mounting on a surface. A tubular body is mounted to the back cover. The tubular body includes an inlet and an outlet for ingress and egress of the fluid through the tubular body. One of the inlet and the outlet includes a valve. An inner cover is attached to the back cover. One or more radiation source is attached to the inner cover. The one or more radiation source produces UV light so arranged relative to the tubular body as to subject the fluid to the UV light. An electronics module is attached to the inner cover and is electrically connected to the valve and the one or more radiation source for controlling operation thereof. A front cover is attached to one of the inner cover and the back cover.

These and other advantages, as well as the invention itself, will become apparent in the details of construction and operation as more fully described and claimed below. Moreover, it should be appreciated that several aspects of the invention can be used in other applications where irradiation of fluids would be desirable.

BRIEF DESCRIPTION OF THE DRAWINGS

FIG. 2 is a perspective view of the present invention shown in FIG. 1;

FIG. 3 is a partial enlarged view one end of the present invention shown in FIG. 1., including one embodiment of a light baffle;

FIG. 8 is a perspective view of an assembled apparatus of one embodiment of the present invention;

FIG. 9 is a perspective view of the apparatus of FIG. 8 with a top cover removed;

FIG. 17 is a perspective view of the internal layout of one embodiment of the present invention.

DETAILED DESCRIPTION OF A PRESENTLY PREFERRED EMBODIMENT

Figure 1:
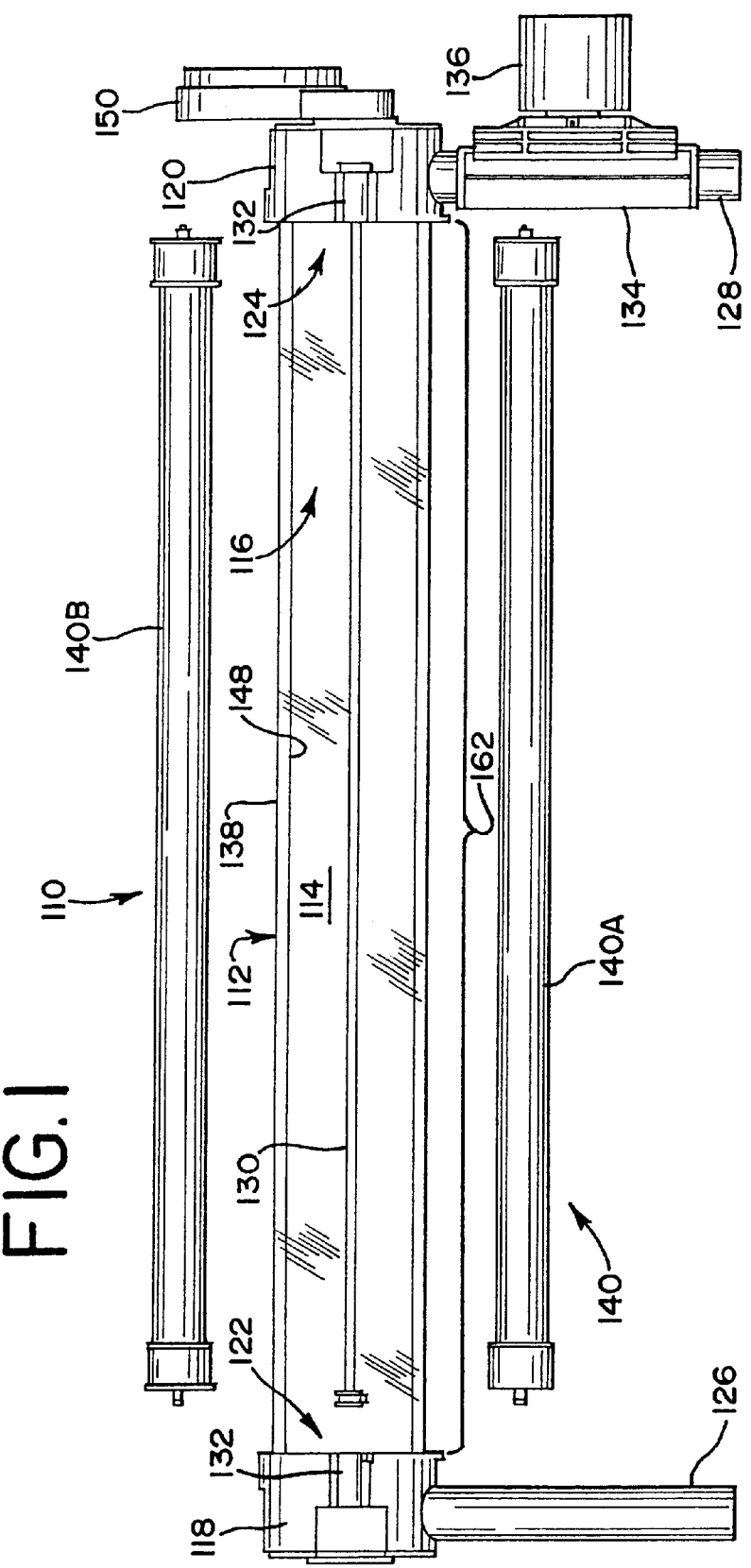
FIG. 1 is a side view of one embodiment of the apparatus of the present invention, including the tubular body with two elongated UV discharge lamps arranged about the tubular body.

An embodiment of the apparatus 110 according to the present invention is illustrated in FIGS. 1–3. It will be understood that the elements of the apparatus 110, described hereinafter, will preferably be contained within a housing (see FIG. 8) made of, for example, stainless steel. The apparatus 110 includes a tubular body 112, an inside surface 148 of which defines a fluid chamber 114, through which a fluid 116 is passed. The tubular body is made of a material that does not significantly reduce transmission of UV light therethrough and is not degraded by UV light. For example, the tubular body 112 is preferably made of quartz in a hollow tube or cylindrical shape.

First and second end caps 118, 120 are positioned to seal against tubular body 112 at first and second open ends 122, 124 of the body. The first and second end caps 118, 120 may be formed of a polymeric material, by injecting molding, for example, a metallic material or any suitable material. The first and second end caps 118, 120 may be drawn together by tie rods 130, which may be inserted into threaded openings 132 of the end caps. A variety of seals (not shown) may be used between the first and second end caps 118, 120 and respective first and second open ends 122, 124, as will be explained below, to prevent fluid loss from fluid chamber 114.

The first cap 118 may include an inlet 126 for receiving fluid 116, which channels the fluid into the fluid chamber 114. The second end cap 120 may include an outlet 128 for permitting fluid 116 to exit the fluid chamber 114 after being irradiated. The second end cap may include a valve 134 and solenoid 136 assembly for controlling the flow of fluid 116 through outlet 128 and thus, through chamber 114.

A UV radiation source 140 is arranged about the outside 138 of the tubular body 112. The source 140, in the illustrated embodiment, may include a pair of UV lamps 140A, 140B designed to emit a high concentration or percentage of ultraviolet light. The UV lamps 140A, 140B are arranged to provide a maximum penetration of UV light through the tubular body 112 and ensure a maximum exposure of the fluid 116 to the emitted UV radiation. The present invention contemplates providing any effective arrangement of UV light sources, which can be a single lamp or a plurality of lamps arranged about the tubular body 112.

The lamps 140A, 140B are easily replaced or removed. This is different from existing devices and enabled by the fact that when the apparatus 110 is wall-mounted (as is typically done), all concentric internal lamps of existing devices require the lamp to be removed axially. Lateral access to the lamps of the present invention is beneficial because it reduces the total amount of space around the unit required for the same length of reactor.

The tubular body 112 is provided a first light baffle 154 and a second light baffle 156 each adjacent a respective end thereof 120, 122 to define an irradiated section 162 of the fluid chamber 114. It can therefore be seen that components of the apparatus 110, positioned outside of the irradiated section 162 are shielded from exposure to UV light by baffles 154, 156. First and second light baffles 154, 156 are preferably made of a material impervious to UV light degradation, such as stainless steel. The light baffles 154, 156 each include a central axial bore 166 for receiving and supporting the shaft 144 and at least one passageway 168 formed therethrough for permitting fluid 116 to pass through each baffle 154, 156, respectively in and out of irradiated section 162 of fluid chamber 114. The passageway 168 may be a single aperture or opening or in the alternate may be a plurality of openings arranged through each baffle 154, 156. The diameter and number of openings constituting passageway 168 may be dictated by the volumetric rate of fluid 116 that flows through the apparatus 110.

A wiper 142 is positioned within the fluid chamber 114 of the tubular body 112 and includes an axial shaft 144. The shaft 144 is a stainless steel rod positioned along the central axis of the fluid chamber 114 and a thin stainless steel blade 146 extending from the shaft 144 to contact an inner surface 148 of the tubular body 112. The wiper 146 serves to keep the inner surface 148 of the tubular body free of foulants and is preferably maintained in constant operation. A motor 150 may be used to rotate the wiper 142. However, other mechanisms may be used as known in the art, such as providing the blade 146 of the wiper 142 in a spiral configuration (not shown) to effect self-rotation. The wiper blade 146 may be provided with a number of features such as a plurality of holes 152 for increased light penetration that allows better treatment of the fluid being conducted. These holes 152 also serve to create turbulence that allows better UV exposure of the fluid being conducted through the chamber 114 by discouraging laminar flow of fluid therethrough. Short perpendicular slits 164 along the length of the blade may be provided to reduce the buildup of stresses and prevent buckling of the blade 146.

Figure 4:
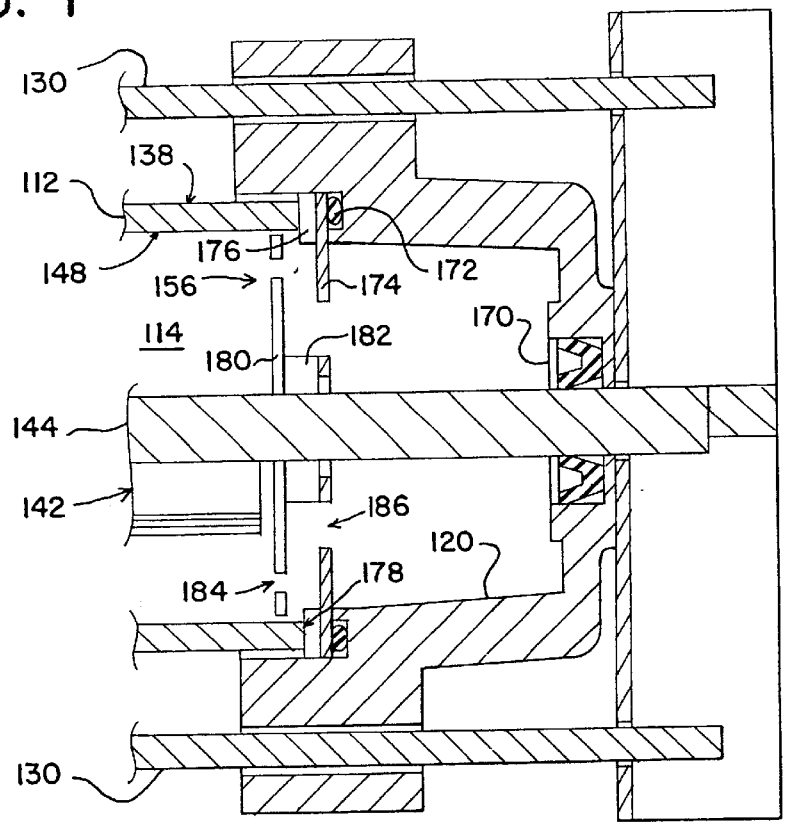
FIG. 4 is a sectional view of one end of the present invention showing another embodiment of a light baffle in place within an end cap.

As best seen in FIG. 4, which includes one embodiment of the light baffle 154 of the present invention, an outer seal 172 may be an o-ring positioned between end cap 120 and outer baffle plate 174. An inner seal 176 may be a flat, annular seal seated between outer baffle plate 174 and end surface 178 of tubular body 112. The pair of tie rods 130 connecting the two end caps 118, 120 together provides compression of these seals 172, 176. In the illustrated embodiment, an inner baffle plate 180 is disposed between outer baffle plate 174 and fluid chamber 114. A spacer 182, or the like, may be used to space inner baffle plate 180 and outer baffle plate 174.

The wiper shaft 144 is supported by bearings 170 positioned outside the fluid chamber adjacent or within end cap 120. In one embodiment, the bearings 170 are fluoropolymer bearings. Positioning the bearings 170 outside of the baffle 156 with respect to the irradiated section 162 (see FIG. 1) of fluid chamber 114 shields the bearings 170, o-ring seal 172 and flat seal 176 from the UV light emitted by the radiation source 140. Fluid flows through baffle 156 by inner openings 184 in inner baffle plate 180 and outer openings 86 in outer baffle plate 174.

Figure 6:
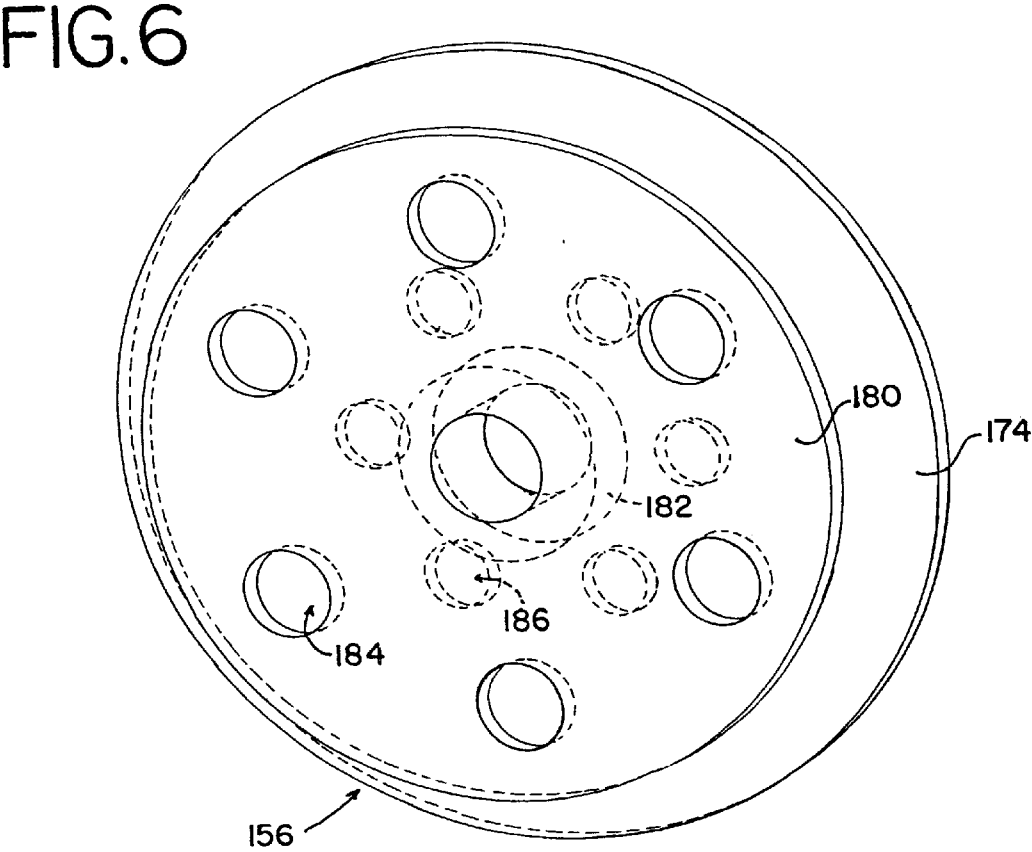
FIG. 6 is one embodiment of a light baffle of the present invention, including a double plate light baffle configuration with holes arranged in an offset pattern to prevent direct light penetration.

The baffle 156 is shown in FIG. 6 including outer and inner baffle plates 174, 180 and inner openings 184 and outer openings 86 (in phantom). Spacer 182 is also shown in phantom for spacing outer and inner baffle plates 174, 180 apart. It can be seen that the inner and outer openings 184, 86 are axially staggered or mis-aligned in order to block the penetration of light therethrough without blocking the flow of fluid.

Figure 7:
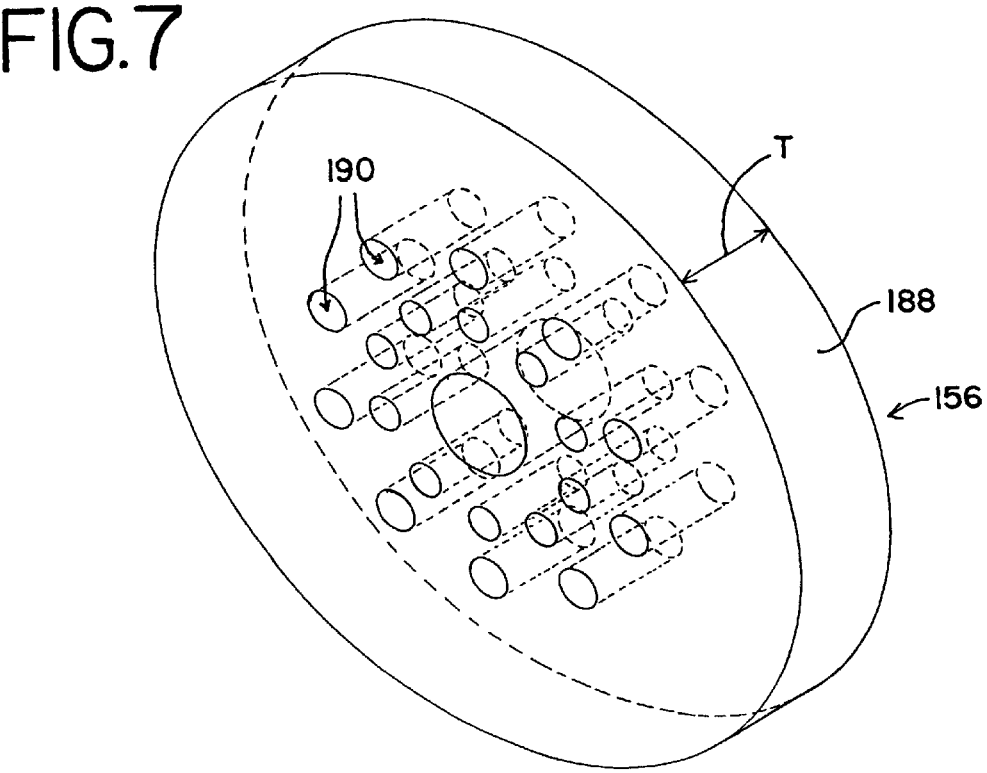
FIG. 7 is another embodiment of a light baffle of the present invention including a single plate with holes having axial bores of a sufficient length to diameter ratio to prevent direct light penetration therethrough.

Another embodiment of the invention includes baffle 156 as shown in FIG. 7, which includes a single plate member 188. The baffle 156 includes one or more passageways 190 formed through the plate member 188. The passageways 190 may be of a relatively lesser diameter and the plate member 188 may be formed in a thickness "T" to prohibit UV light from irradiating the polymeric seals and bearings (not shown).

Figure 5:
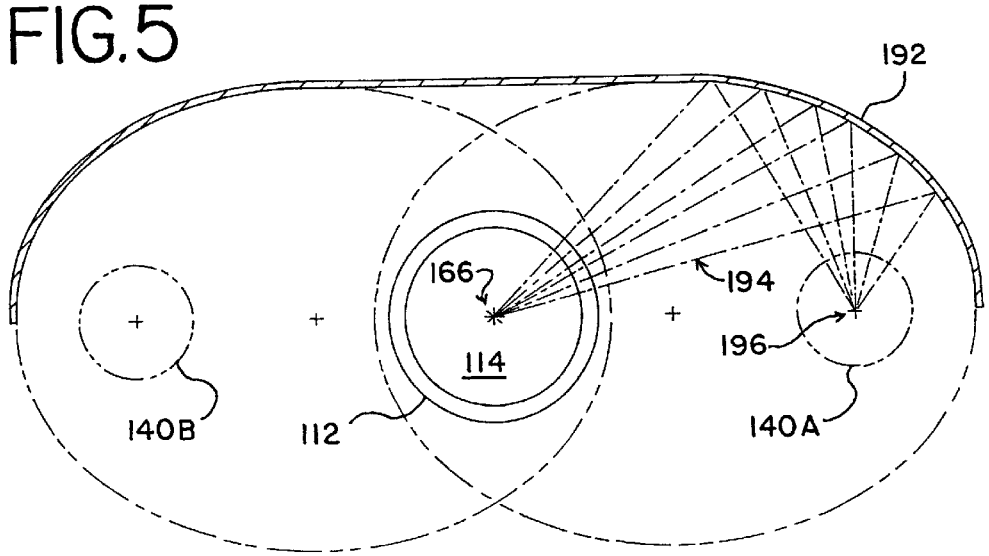
FIG. 5 is an end-view schematic of one embodiment of a reflector showing how light from two UV lamps is reflected and concentrated on a central axis of the tubular body.

An embodiment of the invention includes a plurality of high efficiency reflectors 192, (one is shown) formed in the illustrated embodiment shown in FIG. 5, of two symmetrical parts, which collect and focus scattered light emitted from the lamps 140A, 140B to the center of the tubular body 112 with the use of elliptical geometry. As shown, light rays 194, which originate from axial center 196 of lamp 140A are reflected to axial center 166 of tubular body 112, i.e., the axial center of the fluid chamber 114. In this manner, nearly all of the emitted UV light from lamps 140A; 140B is used in irradiating fluid 116 in fluid chamber 114 of tubular body 112.

An embodiment of the present invention is illustrated in FIGS. 8–17. In the illustrated embodiment, assembled UV sterilization unit 210 is shown in a modular design including a front cover 212 and a back cover 214 to form a housing 216 for the UV sterilization unit 210. The unit includes assembly 110 illustrated above and an electronics module (not shown) for controlling the operation of assembly 110 and other components as will described more fully herein. The unit 210, shown in FIG. 8, may have a rectangular shape defined by front cover 212 and back cover 214. The inlet 126 and outlet 128 are shown extending from a side 218 of the housing.

As shown in FIG. 9, the unit 210 includes assembly 110 positioned within outer cover 212 and back cover 214. An inner cover 220 protects the electronics module that forms the control circuitry (not shown).

Figure 10:
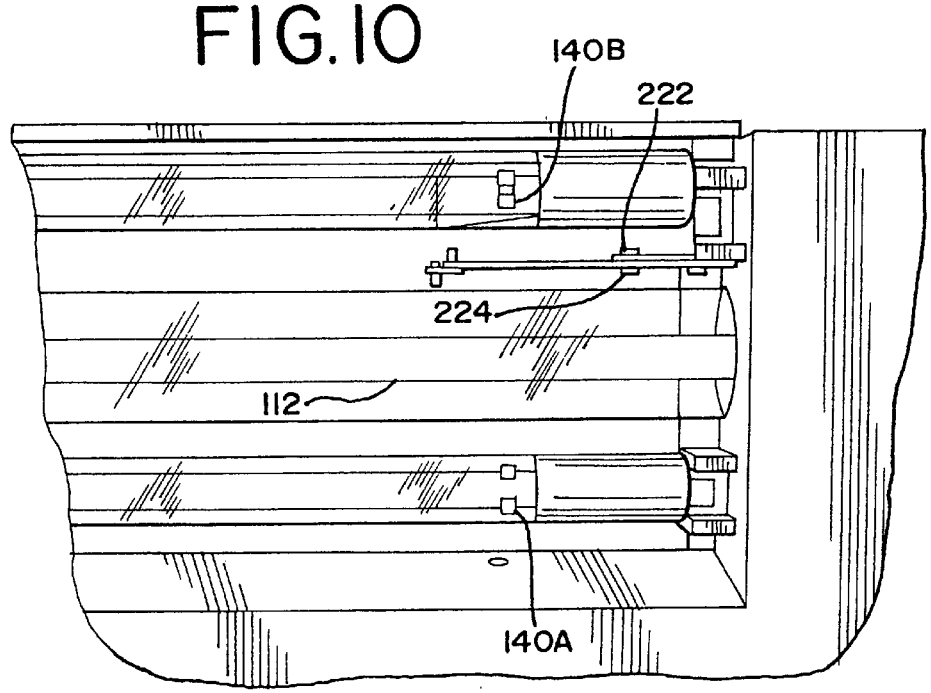
FIG. 10 is a perspective view of the apparatus of FIG. 8 illustrating the light sensors.
Figure 11:
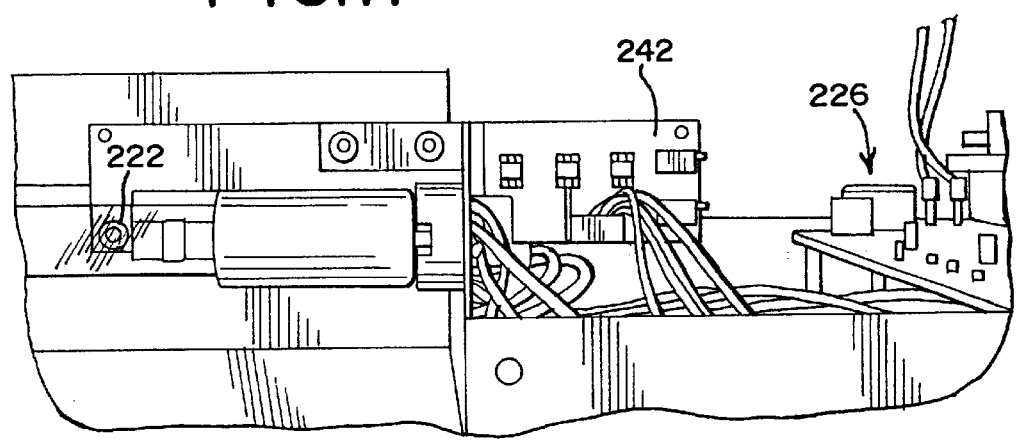
FIG. 11 is another perspective view of the light sensors of FIG. 10 and associated electronics.

As shown in FIGS. 10 and 11, a light sensor 222 may be positioned adjacent one of the radiation sources, for example UV Lamp 140B to measure light output of the radiation source. A second light sensor 224 may be positioned adjacent the tubular body 112 to measure light transmission from the UV Lamp 140A through the tubular body. The light sensors 222, 224 are electrically connected to the electronics module 226 by way of a sensor card 242. The light sensors 222, 224 may be provided to sense when output from a radiation source falls below a preset output level or light transmission through the tubular body 112 falls below a preset level from fouling or the like. The electronic module 226 may be programmed to automatically shut down the unit 210 when the unit does not perform to specification when, for example, a radiation source fails or becomes old and UV light output falls below a specified level or when turbidity increases in the tubular body 112 due to fouling or the like. The electronic module 226 can provide a signal indicating that the assembly 110 has been shut down and requires maintenance.

Figure 12:
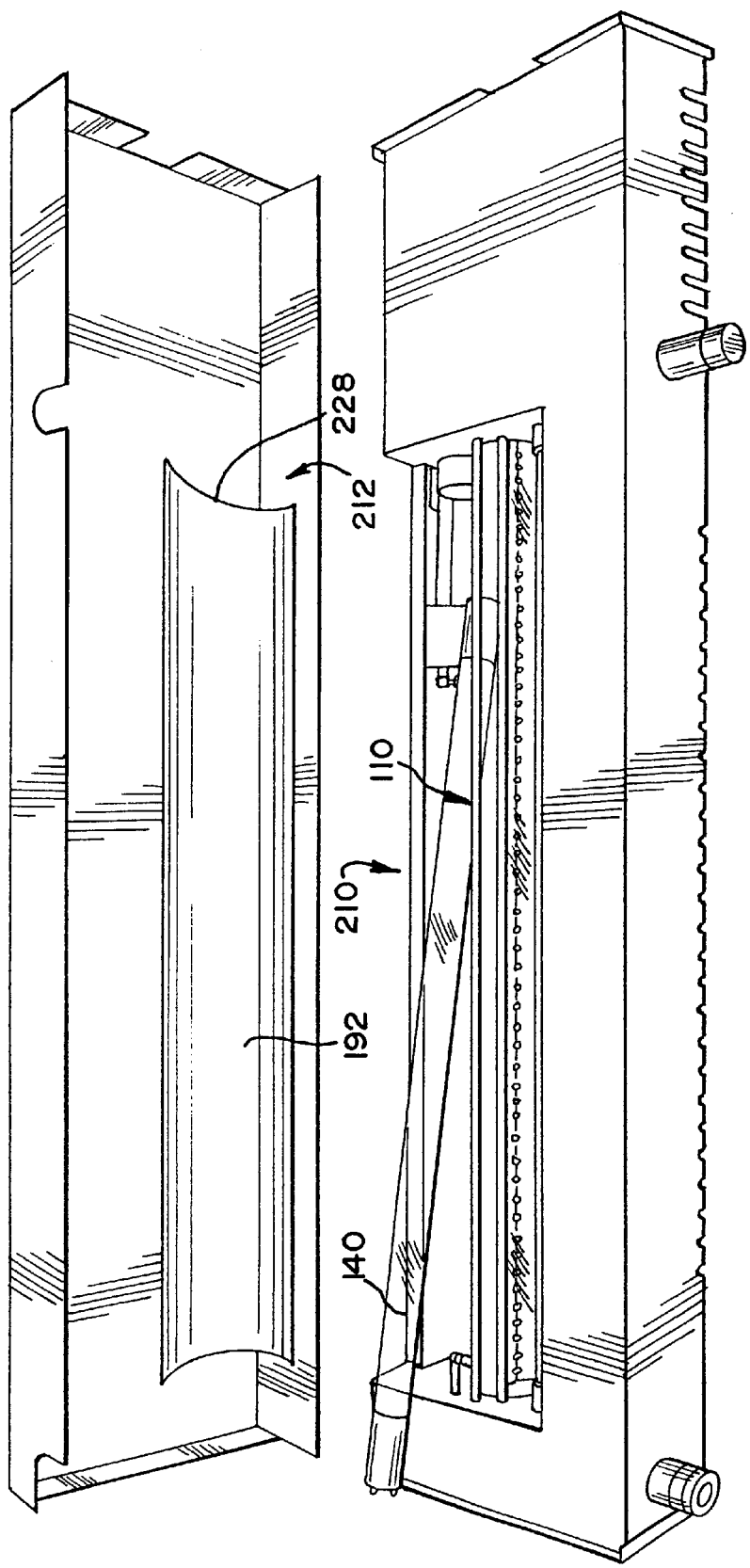
FIG. 12 is a perspective view illustrating the removal of a UV lamp.

The embodiment shown in FIG. 12 illustrates another advantage of the modular design of the unit 210 of the present invention. In the event that a radiation source requires replacement, the front cover 212 may be removed and the radiation source 140 may be pulled from the assembly 110 laterally. For this reason, multiple units of the present invention may be closely positioned aside each other. In the illustrated embodiment one of the reflectors 192 is shown positioned on the inner surface 228 of the front cover 212.

Figure 13:
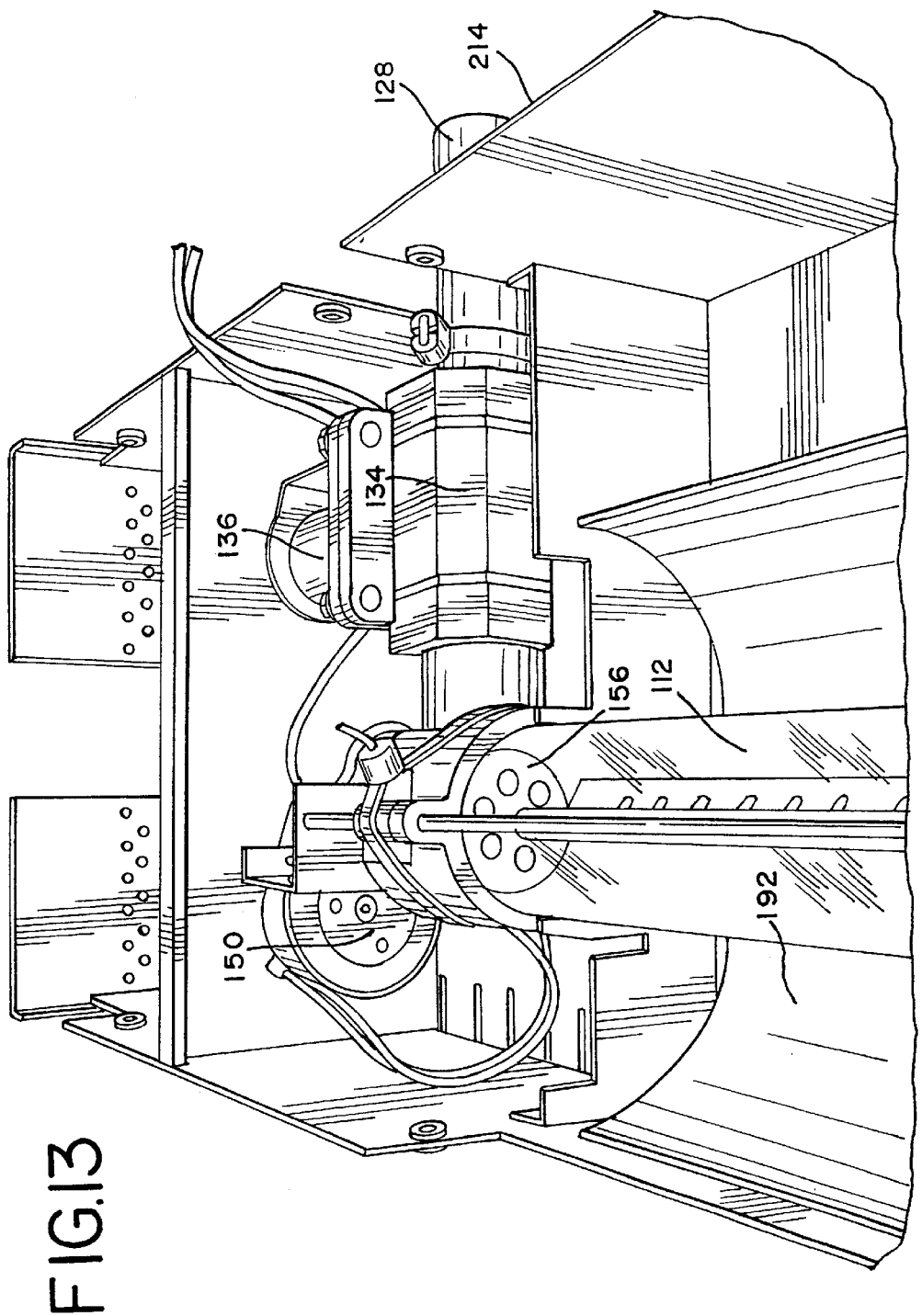
FIG. 13 is a perspective view of the present invention including a light baffle.

The embodiment in FIG. 13 illustrates the back cover 214 including a second reflector 192. Components of the assembly 110 are shown in position, i.e., the tubular body 112 adjacent the reflector 192. The tubular body 112 is held by end cap 120 and tie rod 130. The motor 150 and solenoid 136 are shown associated with the outlet 128 and valve 134. The light baffle 156 is shown in place in the tubular body 112.

Figure 14:
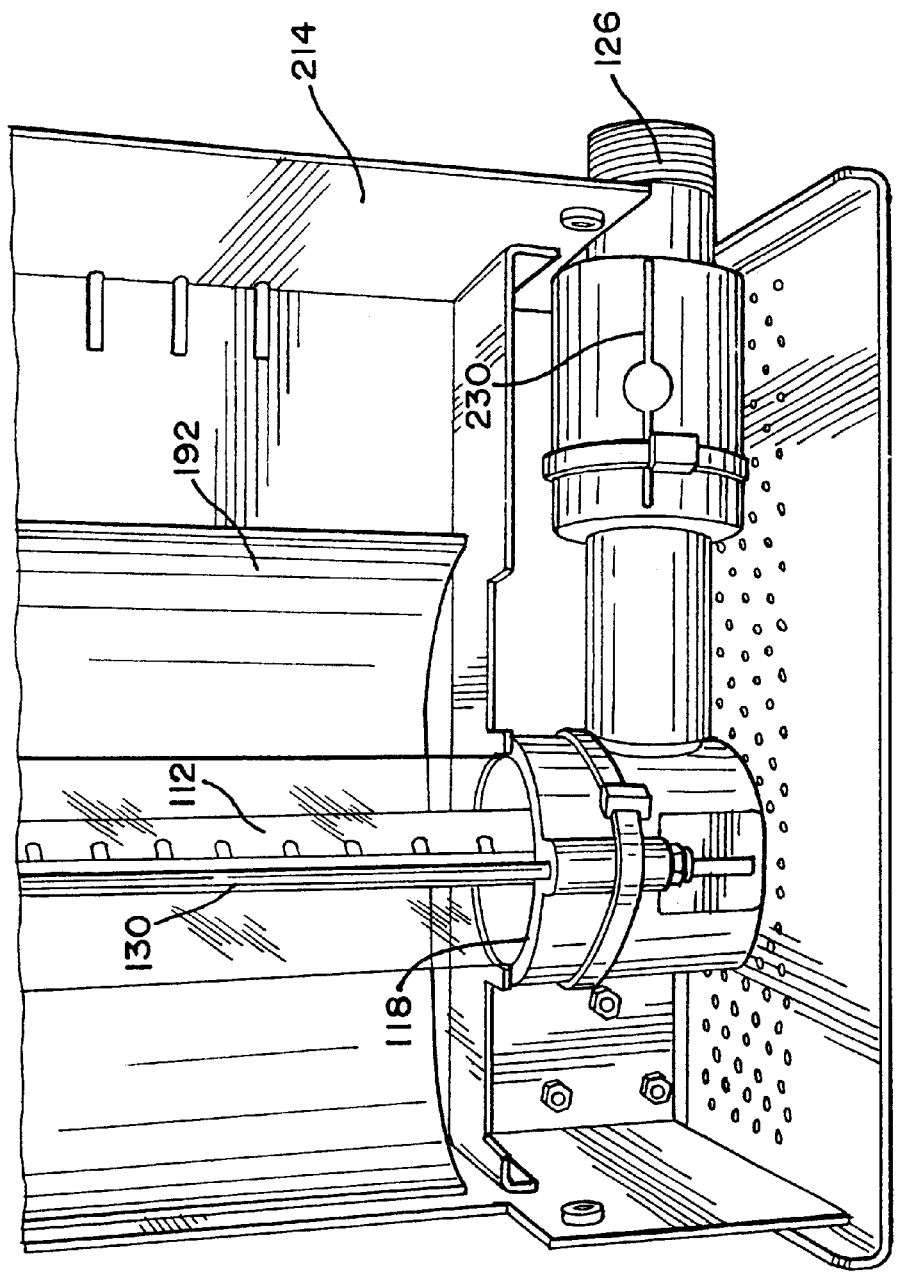
FIG. 14 is a perspective view of an inlet end of the present invention including a flow restrictor.

The embodiment shown in FIG. 14 illustrates a flow restrictor 230 associated with the inlet 126 for restricting the flow of fluid directed into the tubular body 112. The tubular body 112 is held adjacent the reflector 192 in the back cover by end cap 118 and tie rod 130.

Figure 15:
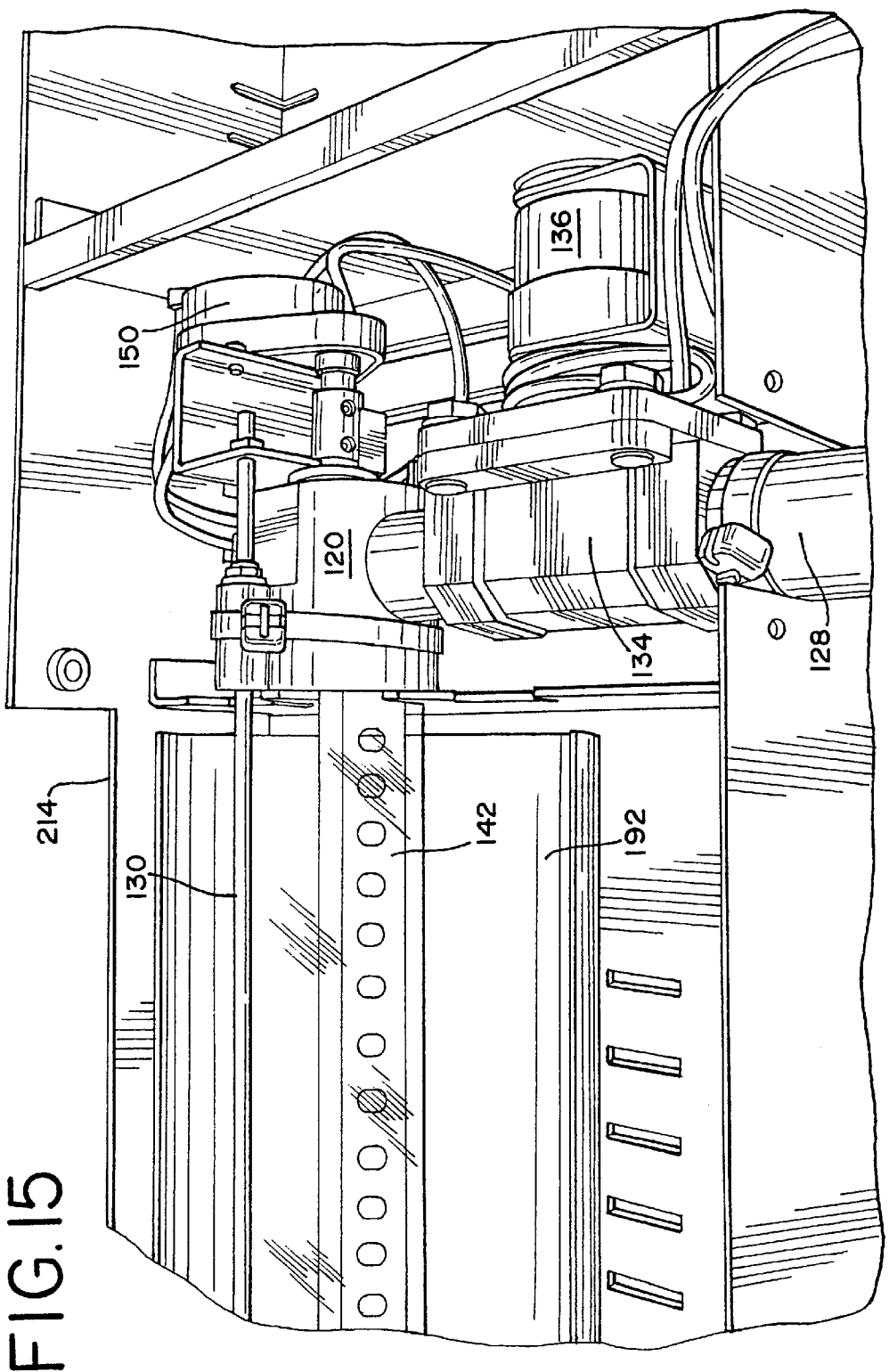
FIG. 15 is a perspective view of an outlet end of the present invention.

The embodiment shown in FIG. 15 includes another view of the outlet end 128. The back cover 214 includes a second reflector 192. Components of the assembly 110 are shown in position, i.e., the tubular body 112 adjacent the reflector 192. The tubular body 112 is held by end cap 120 and tie rod 130. The motor 150 and solenoid 136 are shown associated with the outlet 128 and valve 134. The wiper 142 is shown in place in the tubular body 112.

Figure 16:
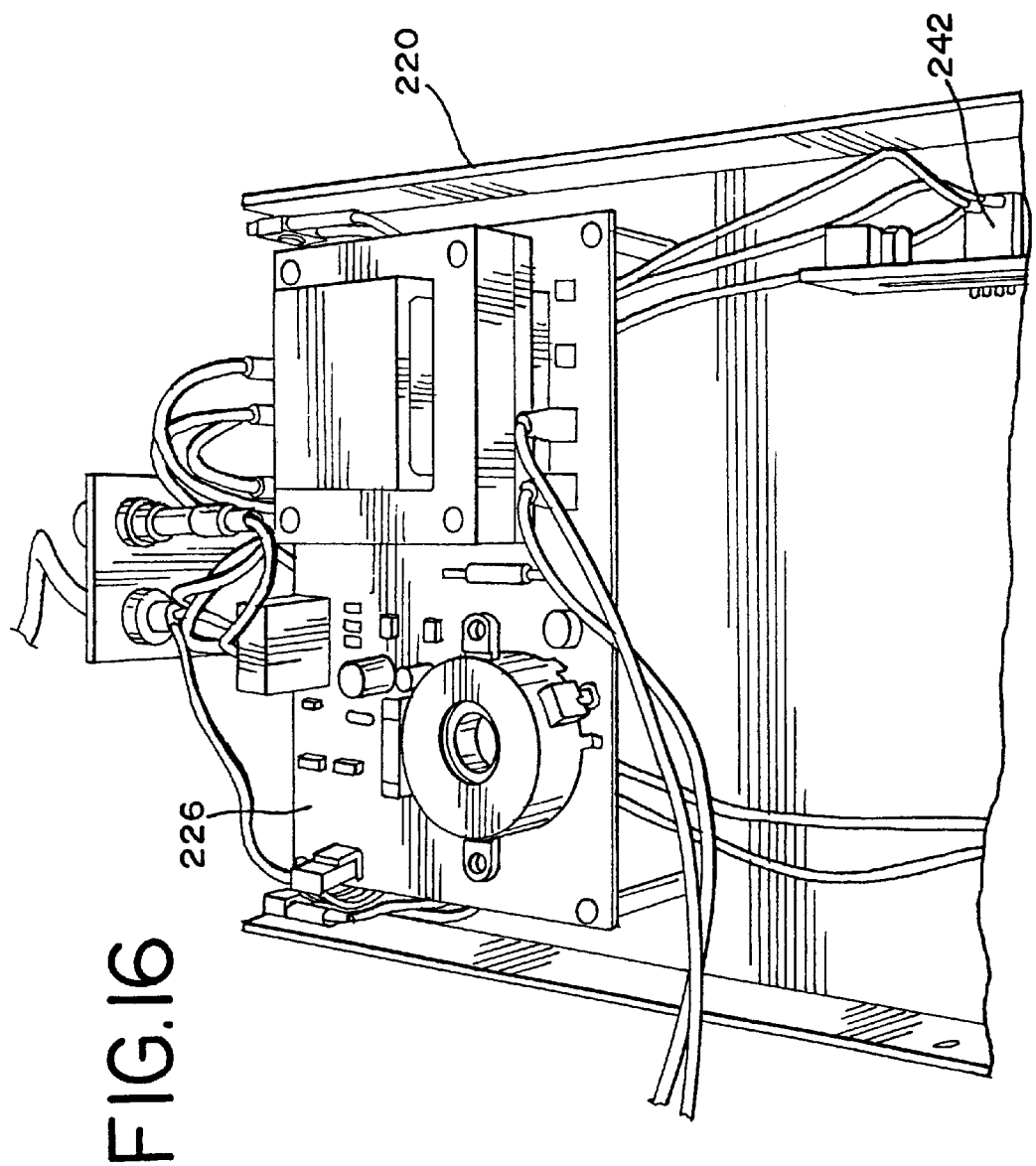
FIG. 16 is a perspective view of the control board of the present invention.

The embodiment shown in FIG. 16 includes the electronics module 226 for controlling operation of the unit 210. It can be seen that in the event that the electronics module 226 needs to be replaced that it can be removed easily and quickly and another module substituted therefore since all of the electronics components reside on a single board. The electronics module 226 is preferably attached to the inner cover 220.

The embodiment shown in FIG. 17 illustrates the four basic modules of the present invention and how the unit 210 is assembled. Back cover 214 may include tubular body 112 and other components associated with assembly 110. Inner cover 220 includes electrical components, such as ballast 240, electronics module 226, light sensor 222 with sensor card 242 and the radiation sources 140 fastened thereto. The inner cover 220 is fastened to back cover 214. The front cover includes reflector 192 and is fastened over inner cover 220 to complete assembly of the unit. The order of assembly may be changed without changing the spirit of the invention. Further, the specific arrangement of components of the unit may be changed into various configurations that contemplate the invention. It can be seen that replacement of any or more than one component of the unit 210 can be performed quickly by virtue of the modular design of the invention and lateral access thereto. It can be seen that maintenance personnel need only detach the front cover 212 to access the radiation sources 140 and remove the radiation sources in a lateral direction. Removal of the inner cover 220 permits access to all of the electronic components 226, 242 and 240 and the remainder of the assembly 110 including the tubular body 112, outlet and inlet 126, 128 and associated components.

While the apparatus and method herein disclosed forms a preferred embodiment of this invention, this invention is not limited to that specific apparatus and method, and changes can be made therein without departing from the scope of this invention, which is defined in the appended claims.

What is claimed is:

1. An apparatus for irradiation of a fluid with UV light comprising:
    a tubular body consisting of a material which is UV-permeable, said tubular body including an inner surface defining a fluid chamber, an open first end and an open second end for ingress and egress of the fluid through said fluid chamber;
    at least one radiation source for producing UV light so arranged relative to said tubular body as to subject said fluid chamber to the UV light;
    a wiper centrally supported in said tubular body for rotation therein, said wiper sized and shaped to contact said inner surface;
    means for rotating said wiper; and
    a first light baffle positioned inside said tubular body adjacent said open first end and a second light baffle positioned inside said tubular body adjacent said open second end, said first and second light baffles defining an irradiated section of said fluid chamber therebetween, said first and second light baffles formed of UV impervious material, each of said first and second light baffles including at least one passageway formed therethrough, said first and second light baffles preventing UV light penetration beyond said irradiated section of said fluid chamber while permitting the fluid to flow through said apparatus.

2. The apparatus of claim 1, wherein said tubular body further includes a first outer end surface adjacent said open first end and a second outer end surface adjacent said open second end.

3. The apparatus of claim 2, further comprising a first end cap and a second end cap, said first end cap contacting said first outer surface and said second end cap contacting said second outer end surface.

4. The apparatus of claim 3, wherein said first end cap includes a fluid inlet in communication with said open first end and said second end cap including a fluid outlet in communication with said open second end.

5. The apparatus of claim 3, wherein a cap seal is positioned between said first outer end surface and a first inner surface of said first end cap and said second outer end surface and a second inner surface of said second end cap.

6. The apparatus of claim 1 wherein said at least one passageway includes at least one hole formed through each respective said first and second light baffles.

7. The apparatus of claim 1, wherein said first and second light baffles are provided in the form of cylindrical plates.

8. The apparatus of claim 7, wherein said first and second light baffles each include a central axial bore formed therethrough for receiving a shaft member of said wiper.

9. The apparatus of claim 1, wherein said wiper includes a blade member sized and shaped to contact said inner surface of said tubular body in said irradiated section thereof.

10. The apparatus of claim 9, wherein said blade member includes at least one hole formed therein.

11. The apparatus of claim 10, wherein said at least one hole is a plurality of holes.

12. The apparatus of claim 1, wherein said first and second light baffles are each a pair of axially aligned cylindrical plates, each of said pair of plates including at least one hole for allowing fluid to pass through said pair of plates, said holes having offset axes such that light is prevented from passing through said first and second light baffles.

13. The apparatus of claim 12, wherein said at least one hole of each said first and second light baffles impart turbulence to flow of the fluid through said first and second light baffles.

14. The apparatus of claim 10, wherein said at least one hole imparts turbulence to flow of the fluid through said tubular body and permits increased UV light penetration into said irradiated section.

15. The apparatus as recited in claim 12, wherein said first and second light baffles are formed of a pair of cylindrical plates having unequal diameters.

16. The apparatus of claim 1, wherein said wiper is formed of a UV impervious material.

17. The apparatus of claim 1, wherein said apparatus is positioned in a chamber including at least one light reflector.

18. The apparatus of claim 1, wherein said wiper includes at least one perpendicular slit to reduce stress buckling of said wiper.

19. The apparatus of claim 8, wherein each said central axial bore includes a bearing for the support of said wiper shaft.

20. The apparatus of claim 19, wherein said bearing is constructed of a fluoropolymer material.

21. The apparatus of claim 8, wherein said first end cap and said second end cap each include a bearing for the support of said wiper shaft.

22. The apparatus of claim 3, wherein a first outer seal is positioned between said first end cap and said first light baffle and a second outer seal is positioned said second end cap and said second light baffle.

23. The apparatus of claim 2, wherein a first inner seal is positioned between said first light baffle and a first outer end surface and a second inner seal is positioned between said second light baffle and a second outer end surface.

24. An apparatus for irradiation of a fluid with UV light comprising:

a back cover for mounting on a surface;

a tubular body mounted to said back cover, said tubular body including an inlet and an outlet for ingress and egress of the fluid through said tubular body, one of said inlet and said outlet including a valve;

an inner cover attached to the back cover;

one or more radiation source attached to said inner cover, said one or more radiation source for producing UV light so arranged relative to said tubular body as to subject the fluid to the UV light;

a first light baffle positioned inside said tubular body adjacent said inlet and a second light baffle positioned inside said tubular body adjacent said outlet, said first and second light baffles defining an irradiated section of said tubular body therebetween, said first and second light baffles formed of UV impervious material, each of said first and second light baffles including at least one passageway formed therethrough, said first and second light baffles preventing UV light penetration beyond said irradiated section of said tubular body while permitting the fluid to flow through said apparatus;

an electronics module electrically connected to said valve and said one or more radiation source for controlling operation thereof; and a front cover attached to one of said inner cover and said back cover.

* * * * *